(12) United States Patent
Nakata

(10) Patent No.: US 11,137,405 B2
(45) Date of Patent: Oct. 5, 2021

(54) LUNG CANCER DETECTION METHOD AND DETECTION KIT

(71) Applicant: TOSOH CORPORATION, Shunan (JP)

(72) Inventor: Daisuke Nakata, Ayase (JP)

(73) Assignee: TOSOH CORPORATION, Yamaguchi (JP)

( * ) Notice: Subject to any disclaimer, the term of this patent is extended or adjusted under 35 U.S.C. 154(b) by 124 days.

(21) Appl. No.: 16/302,413

(22) PCT Filed: May 10, 2017

(86) PCT No.: PCT/JP2017/017723
§ 371 (c)(1),
(2) Date: Nov. 16, 2018

(87) PCT Pub. No.: WO2017/199817
PCT Pub. Date: Nov. 23, 2017

(65) Prior Publication Data
US 2019/0277853 A1    Sep. 12, 2019

(30) Foreign Application Priority Data
May 18, 2016  (JP) .............................. JP2016-099312

(51) Int. Cl.
*G01N 33/574* (2006.01)
*C12N 9/16* (2006.01)

(52) U.S. Cl.
CPC ..... *G01N 33/57469* (2013.01); *G01N 33/574* (2013.01); *C12N 9/16* (2013.01)

(58) Field of Classification Search
None
See application file for complete search history.

(56) References Cited

U.S. PATENT DOCUMENTS

2009/0324617 A1   12/2009   Satomaa et al.
2016/0109452 A1    4/2016   Chen et al.

FOREIGN PATENT DOCUMENTS

EP    2 860 250 A1    4/2015
JP    2016-042083 A    3/2016
(Continued)

OTHER PUBLICATIONS

Nakata, D. et al., Scientific Reports, Oct. 22, 2014, vol. 4, No. 6715, pp. 1-8 (Year: 2014).*

(Continued)

*Primary Examiner* — Karl J Puttlitz
(74) *Attorney, Agent, or Firm* — Sughrue Mion, PLLC

(57) ABSTRACT

Lung cancer can be detected by measuring sites in pancreatic ribonuclease 1 (also abbreviated as "RNase 1"), wherein each of the sites is a site capable of being modified with an N-linked sugar chain. Lung cancer is detected by measuring items A and B as mentioned below and then comparing the ratio of the value of A to the value of B: A=the amount of sites in pancreatic ribonuclease 1, wherein the sites are sites each capable of being modified with an N-linked sugar chain and each having an N-linked sugar chain bound thereto or each having an N-linked sugar chain unbound thereto; and B=the amount of sites in pancreatic ribonuclease 1, wherein the sites are sites each capable of being modified with an N-linked sugar chain.

3 Claims, 3 Drawing Sheets

Specification includes a Sequence Listing.

(56) References Cited

FOREIGN PATENT DOCUMENTS

| JP | 2016042083 | * | 3/2016 |
| KR | 10-2011-0076830 A | | 7/2011 |
| WO | 03/060522 A1 | | 7/2003 |
| WO | 2006/114659 A1 | | 11/2006 |
| WO | 2007/010089 A2 | | 1/2007 |
| WO | 2007010089 | * | 1/2007 |
| WO | 2007/132967 A1 | | 11/2007 |
| WO | 2013187371 | * | 12/2013 |

OTHER PUBLICATIONS

Machine Translation of WO 2013187371, Google Patents, downloaded Jul. 10, 2020 (Year: 2013).*
Machine Translation of JP 2016042083, Google Patents, downloaded Jul. 10, 2020 (Year: 2016).*
Communication dated Jan. 9, 2020 from European Patent Office in EP Application No. 17799242.7.
International Search Report for PCT/JP2017/017723, dated Jun. 27, 2017.

* cited by examiner

SEQUENCE LISTING

```
<160> NUMBER OF SEQ ID NOS: 1

<210> SEQ ID NO 1
<211> LENGTH: 128
<212> TYPE: PRT
<213> ORGANISM: Homo sapiens

<400> SEQUENCE: 1

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125
```

LUNG CANCER DETECTION METHOD AND DETECTION KIT

CROSS REFERENCE TO RELATED APPLICATIONS

This Application is a National Stage of International Application No. PCT/JP2017/017723 filed May 10, 2017, claiming priority based on Japanese Patent Application No. 2016-099312 filed May 18, 2016 are incorporated herein by reference as if fully set forth in their entireties.

FIELD

The present invention relates to a method for detecting lung cancer and a kit for detecting the same. More particularly, the present invention relates to a method for detecting lung cancer by measuring the presence or absence of a glycan chain linked to a site capable of being modified by an N-glycan chain in pancreatic ribonuclease 1 (referred to as "RNase 1" hereinbelow) and a detecting kit thereof.

BACKGROUND

A large number of patients are suffering from lung cancer. According to Non-Patent Document 1 and Non-Patent Document 2, the number of these patients suffered in 2011 was about 110,000 in Japan, and was the second largest after gastric cancer. The death toll was about 70.000 and was the largest. Lung cancer is often detected and diagnosed by imaging diagnostic methods represented by X-ray imaging. The detection limit and sensitivity thereof depend on the skill of the radiographer and the image capturing device. The detection of a small tumor tissue such as early cancer is considered difficult. Blood tumor markers used in the clinical practice of lung cancer are not used for the detection of lung cancer due to the low positive rates thereof, but are exclusively used for the monitoring of therapeutic effects.

RNase 1 in the blood is considered to be a protein which is produced mainly in the pancreas and secreted into the bloodstream. There are also some reports which suggest the expression thereof in tissue other than the pancreas. However, the expression of RNase 1 in lung tissue has remained to be elucidated in detail. Patent Document 1 demonstrates that glycosylation, which is not observed in healthy individuals, is increased at specific asparagine residues of RNase 1 in the blood obtained from patients with pancreatic cancer, and discloses a method for the detection of pancreatic cancer. Patent Document 2 describes a method for accurately measuring the amount of glycosylation at 88th asparagine residue (hereinafter, referred to sometimes as "Asn88") of RNase 1 described previously and the results of measurements in pancreatic cancer, gastric cancer, and cholangiocarcinoma. However, these Patent Documents do not describe the expression of RNase 1 in lung cancer, let alone the detection of glycosylation at Asn88 of RNase 1 in lung cancer. As described above, RNase 1 in the blood and a change in glycosylation at a specific asparagine residue have not been measured for the purpose of the detection of lung cancer.

There are four types (adenocarcinoma, non-small cell carcinoma, small cell carcinoma, and squamous cell carcinoma) of cancer occurring in the lung, depending on the tissue type. There are markers used for the respective tissue types in low-invasive blood testing for the detection of lung cancer. However, due to the low positive rates thereof, they are not used for screening, etc. The measurement of these markers is not recommended as the "first step for the purpose of the detection of lung cancer" in the "Clinical Guidelines for the Management of Lung Cancer 2016" by the Japan Lung Cancer Society. The "first step for the purpose of the detection of lung cancer" recommended in the "Clinical Guidelines for the Management of Lung Cancer 2016" is a chest radiograph. Chest radiography is a popular detection technique in Japan, but there is a risk of exposure to radiation, and chest radiography is a detection method which is highly invasive compared to blood testing, etc. In order to overcome lung cancer, a marker which can be detected regardless of the tissue type is considered to be necessary.

PRIOR ART DOCUMENTS

Patent Documents

Patent Document 1: WO2013/1187371
Patent Document 2: JP2016-042083A

Non-Patent Documents

Non-Patent Document 1: Vital Statistics, Statistics and Information Dept., Minister's Secretariat, Ministry of Health, Labour and Welfare, Sep. 6, 2012
Non-Patent Document 2: Japanese Journal of Clinical Oncology, 44(4): 388-396, 2013. Cancer Information Service, National Cancer Center, Japan, "Cancer Registry and Statistics"

DISCLOSURE OF THE INVENTION

Problems to be Solved by the Invention

An object of the present invention is to provide a method for detecting lung cancer by focusing on putative N-glycosylation sites of RNase 1.

Means for Solving the Problems

As a result of conducting extensive studies to solve the aforementioned problems of the present invention, the inventor of the present invention found that cases in which glycan chains are linked to putative N-glycosylation sites of RNase 1 increase in lung cancer patients in comparison with healthy individuals, thereby leading to completion of the present invention.

Namely, the present invention is as indicated below.

(1) A method for detecting lung cancer, characterized by measuring the amount of a putative N-glycosylation site of RNase 1 linked with an N-glycan chain or not linked with an N-glycan chain.

(2) The method according to (1), wherein the amount of the site linked with the N-glycan chain is increased in comparison with healthy individuals.

(3) A method for detecting lung cancer, comprising: determining the ratio of the value of A to the value of B for A and B indicated below:
   A: amount of putative N-glycosylation site of RNase 1 linked with an N-glycan chain or not linked with an N-glycan chain; and,
   B: amount of putative N-glycosylation site of RNase 1.

(4) The method according to (3), wherein A represents the amount of the site not linked with an N-glycan chain, and the value of A/B is smaller in comparison with healthy individuals.

(5) The method according to (3), wherein A represents the amount of the site linked with an N-glycan chain, and the value of A/B is larger in comparison with healthy individuals.

(6) The method according to any of (3) to (5), wherein the amount of RNase 1 is determined and that value is converted to use as the value of B.

(7) The method according to any of (1) to (6), wherein the putative N-glycosylation site is asparagine residue at position 88 of the sequence indicated in SEQ ID NO: 1.

(8) A kit for detecting lung cancer, comprising monoclonal antibody, or fragment thereof, recognizing a putative N-glycosylation site of RNase 1 as a portion of the antigen recognition site thereof.

The following provides a more detailed explanation of the present invention. The present invention detects lung cancer by measuring the amount of a putative N-glycosylation site in RNase 1 linked with an N-glycan chain or not linked with an N-glycan chain. At this time, the amount of the putative N-glycosylation "site" in RNase 1 linked with the N-glycan chain or the amount of the "site" not linked with an N-glycan chain is measured, while the amount of a "glycan chain" linked to the putative N-glycosylation site is not measured.

RNase 1 as a subject of measurement is preferably derived from a human biological sample. As a result of using this as a measurement subject, human lung cancer can be detected. At this time, since there are many cases in which an N-glycan chain is linked to a putative N-glycosylation site in lung cancer patients in comparison with healthy individuals, and there is an increase in the amount of the putative N-glycosylation site linked with the N-glycan chain, lung cancer can be detected by using this as an indicator.

In addition, the present invention is a method for detecting lung cancer that includes the determination of the ratio of the value of A to the value of B for A and B as indicated below:

A: amount of putative N-glycosylation site in RNase 1 linked with an N-glycan chain or not linked with an N-glycan chain; and, B: amount of putative N-glycosylation site in the RNase 1.

In addition, a method is preferably used in which A represents the amount of the site not linked with an N-glycan chain, and the value of A/B is smaller in comparison with healthy individuals. In addition, a method is also preferably used in which A represents the amount of the site where N-glycan chain is bound, and the value of A/B is larger in comparison with healthy individuals.

In the case B represents the amount of a putative N-glycosylation site of RNase 1, there are no particular limitations on the determination method thereof, and for example, the amount of RNase 1 can be determined followed by converting that value to use as the value of B. More specifically, since RNase 1 has three putative N-glycosylation sites (asparagine residues at positions 34, 76 and 88 of SEQ ID NO: 1), when the amount of any one, two or all of these sites is used as the measurement subject, the amount of the putative N-glycosylation site of RNase 1 represented by B can be respectively converted to 1 time, 2 times or 3 times the amount of RNase 1 corresponding thereto. Furthermore, the amount of RNase 1 can be determined by method such as that using an immunological assay method or mass spectrometry.

Furthermore, RNase 1 has three putative N-glycosylation sites (asparagine residues at positions 34, 76 and 88 of SEQ ID NO: 1) as previously described. Since a remarkable difference in values is observed between lung cancer patients and healthy individuals if the aforementioned amount is measured as the amount of the putative N-glycosylation site with respect to the asparagine residue at position 88 of SEQ ID NO: 1 in particular, this is preferable as a method for detecting lung cancer.

Further, the method and the kit of the present invention can detect all of the four tissue types (adenocarcinoma, non-small cell carcinoma, small cell carcinoma, and squamous cell carcinoma) of lung cancer, and can detect lung cancer regardless of the tissue type.

When lung cancer is detected by the present invention, it is preferable that a treatment thereof be appropriately performed. The treatment method is not particularly limited and may be appropriately selected from methods for the treatment of lung cancer.

Effects of the Invention

According to the present invention, lung cancer can be detected. In addition, all of four tissue types of lung cancer can be detected.

EXAMPLES

Example 1: Amount of Asn88 at which an N-Glycan Chain is Linked, Amount of Asn88, and Ratio Thereof in Serum Samples Derived from Patients with Lung Cancer The putative N-glycosylation site to be measured was designated Asn88. The amount of Asn88 at which an N-glycan chain is linked (G3), and the amount of Asn88 (t) were measured using the immunological assay reagents and the assay described in Examples 3 and 4 of Patent Document 2, respectively. Thirty-five serum samples obtained from healthy individuals and 40 serum samples obtained from patients with lung cancer were measured using the above immunological assay reagents. In this Example, the amount of the putative N-glycosylation site Asn 88 can be calculated as a value which is one time the total amount of RNase 1. The results are shown in Table 1 and FIG. 1.

TABLE 1

| | Healthy individuals (average and distribution range) | Patients with lung cancer (average and distribution range) | P value |
|---|---|---|---|
| Number of samples | 35 | 40 | |
| Age Distribution | 38 (27 to 62) | 69 (48 to 78) | |
| Amount (t) of Asn88 | 256.09 (151.91 to 369.48) | 250.95 (122.12 to 846.88) | 0.54 |
| Amount (G3) of | 29.44 | 93.02 | <0.05 |

TABLE 1-continued

| | Healthy individuals (average and distribution range) | Patients with lung cancer (average and distribution range) | P value |
|---|---|---|---|
| Asn88 at which an N-glycan chain is linked | (16.1 to 48.13) | (49.49 to 259.49) | |
| G3/t ratio | 0.11 (0.1 to 0.13) | 0.3 (0.24 to 0.6) | <0.05 |

Figure 1:
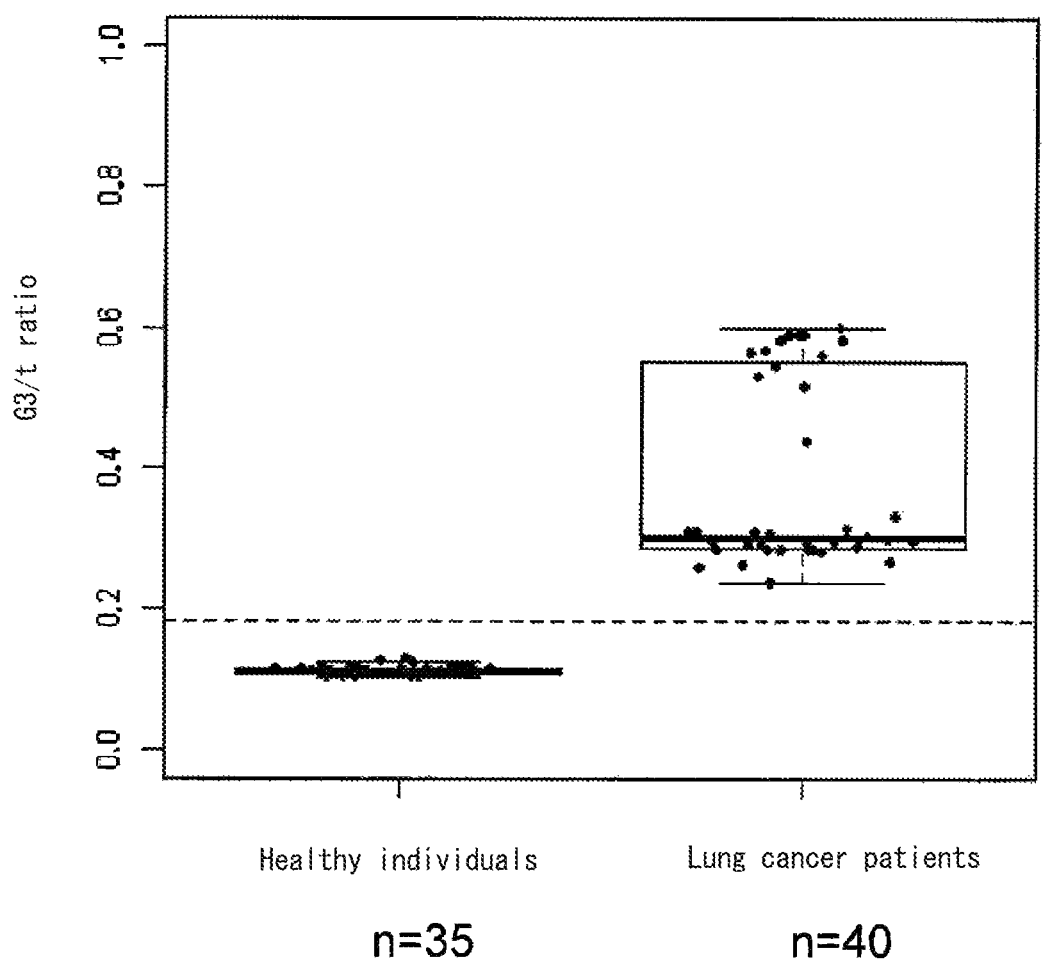
FIG. 1 is a graph illustrating the distributions of G3/t ratios of healthy individuals and patients with lung cancer, wherein the dashed line represents a cut-off value, 0.184.

As shown in Table 1 and FIG. 1, both of the G3 and the G3/t ratio of the lung cancer patient serum were significantly higher than those of healthy individual group (p<0.05 in both cases). These results demonstrated that lung cancer can be detected by measuring G3 or the G3/t ratio.

Figure 2:
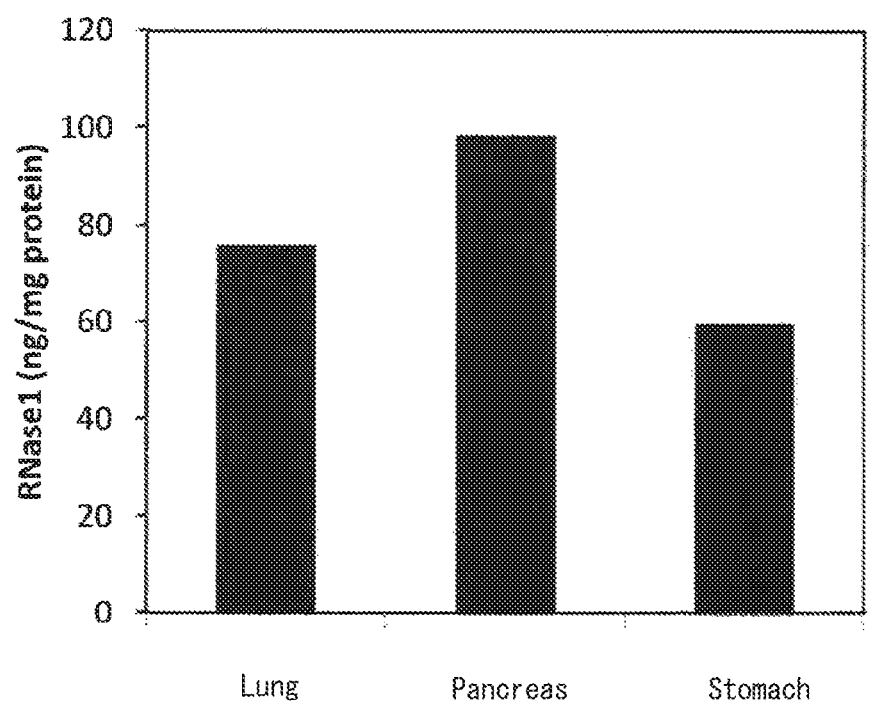
FIG. 2 is a drawing illustrating the results of total RNase 1 amounts in extracts from normal human tissue.

Example 2: Verification of the Expression of RNase 1 in Normal Human Lung Tissue Homogenates of normal human lung tissue, tissue extracts of normal human pancreatic tissue, tissue extracts of normal human stomach tissue were obtained from BioChain, Inc. The total RNase 1 amounts of these extracts were measured by the above immunological assay. As illustrated in FIG. 2, the expression of RNase 1 was verified even in normal human lung tissue. Thus, the reason that the cancerous change of lung tissue changed the level of the linkage of N-glycan chain at Asn88 of RNase 1 in the bloodstream was considered to be the enhancement of the linkage of N-glycan chain at Asn88 during the novel biosynthetic process of RNase 1 expressed in lung cancer cells.

Figure 3:
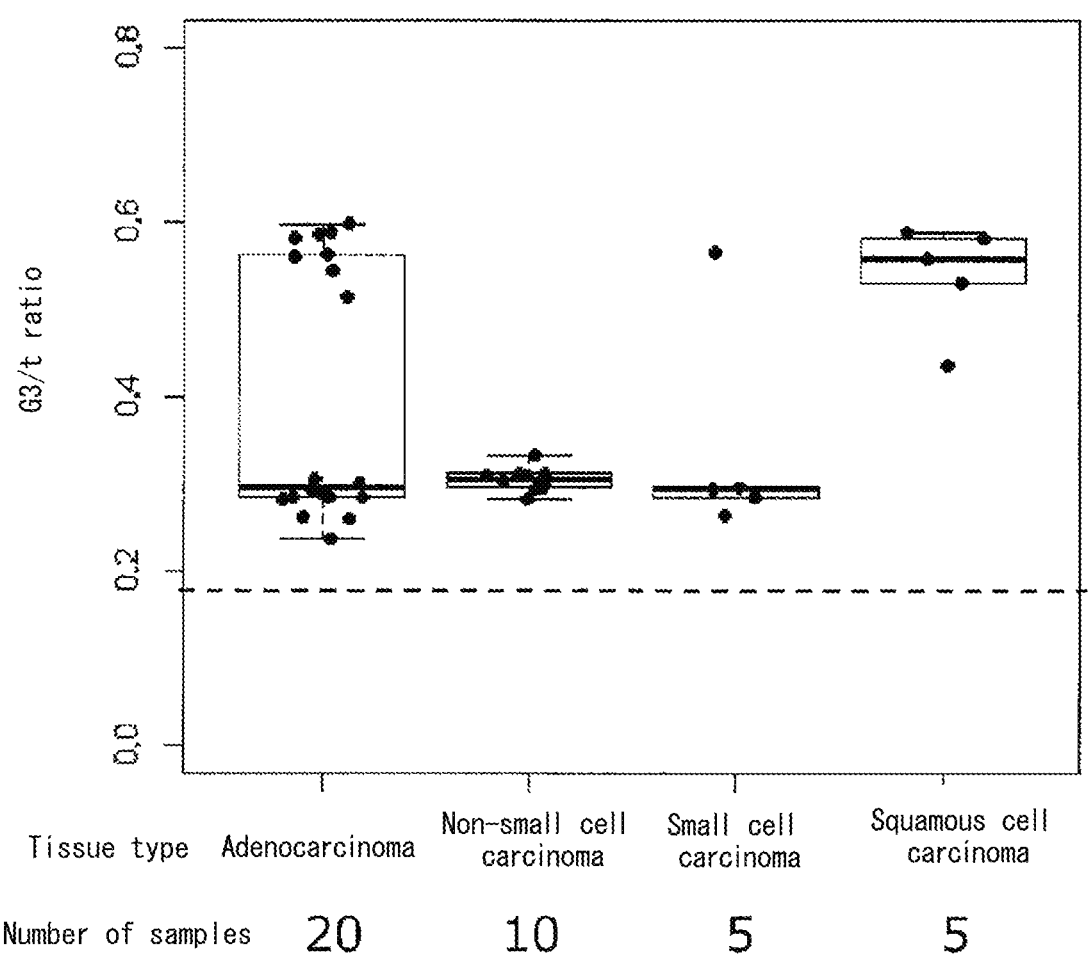
FIG. 3 is a drawing illustrating the distributions of G3/t ratios of tissue types of lung cancer, wherein the dashed line represents a cut-off value, 0.184.

Example 3: Analysis of the Distributions of G3/t Ratios of Tissue Types of Lung Cancer The 40 serum samples (which were able to be histologically diagnosed) obtained from patients with lung cancer were measured using the immunological assay reagents and the assay described in Example 1. The results are plotted for each tissue type in FIG. 3. As is clear from FIG. 3, all of the ratios of each of the four tissue types exceeded the cut-off value 0.184. These results in combination with the results illustrated in FIG. 1 demonstrated that all of the four types of lung cancer were uniformly detected without a deviation in the four tissue types using the above mentioned immunological assay reagents and the assay, and thus, suggested that the immunological assay reagents and the assay are excellent in the detection of a wide variety of types of lung cancer.

The contents of the specification, sequence listing, claims, drawings, and abstract of the Japanese Patent Application No. 2016-099312 filed on May 18, 2016 are incorporated herein by reference as if fully set forth in their entireties.

The invention claimed is:

1. A method for detecting and treating lung cancer in a subject, comprising:
    measuring the amount of a putative N-glycosylation site of pancreatic ribonuclease 1 linked with an N-glycan chain or not linked with an N-glycan chain using an immunological method in a subject suspected of having lung cancer,
    diagnosing the subject with lung cancer if the amount of the site linked with the N-glycan chain is increased in comparison with healthy individuals, and
    treating the subject with lung cancer with a method for the treatment of lung cancer,
    wherein the putative N-glycosylation site is asparagine residue at position 88 of the sequence indicated in SEQ ID NO: 1.

2. A method for detecting and treating lung cancer in a subject, comprising:
    determining the ratio of the value of A to the value of B for A and B indicated below:
    A: amount of putative N-glycosylation site of pancreatic ribonuclease 1 linked with an N-glycan chain or not linked with an N-glycan chain measured using an immunological method in a subject suspected of having lung cancer; and,
    B: amount of putative N-glycosylation site of pancreatic ribonuclease 1 measured using an immunological method in a subject suspected of having lung cancer,
    diagnosing the subject with lung cancer if the value of A/B is smaller in comparison with healthy individuals when A represents the amount of the site not linked with an N-glycan chain or if the value of A/B is larger in comparison with healthy individuals when A represents the amount of the site linked with an N-glycan chain, and
    treating the subject with lung cancer with a method for the treatment of lung cancer,
    wherein the putative N-glycosylation site is asparagine residue at position 88 of the sequence indicated in SEQ ID NO: 1.

3. The method according to claim 2, wherein the amount of pancreatic ribonuclease 1 is determined and that value is converted to use as the value of B.

* * * * *